(12) United States Patent
Livi et al.

(10) Patent No.: US 6,909,029 B2
(45) Date of Patent: Jun. 21, 2005

(54) CAENORHABDITIS ELEGANS CHEMOSENSORY BIOASSAY FOR SEVEN TRANSMEMBRANE RECEPTOR LIGANDS

(75) Inventors: George P. Livi, King of Prussia, PA (US); Christopher Shelton, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 97 days.

(21) Appl. No.: 09/963,990

(22) Filed: Sep. 26, 2001

(65) Prior Publication Data

US 2002/0124275 A1 Sep. 5, 2002

Related U.S. Application Data

(60) Provisional application No. 60/237,290, filed on Oct. 2, 2000.

(51) Int. Cl.[7] .......................... G01N 33/00; A01K 67/00; A01K 67/033
(52) U.S. Cl. ............................................. 800/3; 800/13
(58) Field of Search ................................ 800/3, 13, 21, 800/25; 435/325, 348

(56) References Cited

FOREIGN PATENT DOCUMENTS

WO          WO 98/53856          12/1998

OTHER PUBLICATIONS

Link et al. Transgenic invertebrate models of age–associated neurodegenerative diseases. Mechanisms of Ageing and Development. 2001, vol. 122, pp. 1639–1649.*

Tobin, et al., "Roles of osm–9/ Capsaicin Receptor Family Members In Sensory Behaviors "*West Coast Worm Meeting, Abstract 20* (2000). This document is only available electronically, and the URL for it is (http://elegans.swmed.edu/wli/[wcwm2000p20]).

Stadel, et al., "Orphan G protein–coupled receptors: a neglected opportunity for pioneer drug discovery," *TiPS, 18*: 430–437 (1997).

Tobin, et al., "Combinatorial Expression of TRPV Channel Proteins Defines Their Sensory Functions and Subcellular Localization in *C. elegans* Neurons," *Neuron, 35*: 307–318 (2002).

Probst, et al., "Sequence Alignment of the G–Protein Coupled Receptor Superfamily," DNA and *Cell Biology, 11(1)*: 1–20 (1992).

Wedel, et al., "New insights on the functions of the guanylyl cyclase receptors," FEBS *Letters, 410(1)*: 29–33 (1997).

Murphy, et al., "Functional studies on the FAX–1 nuclear receptor," Internet Article, East Coast Worm Meeting Abstract 157, Online! 2000, Retrieved from the Internet, URL http://elegans.swmed.edu.

Jansen, et al., "The complete family of genes encoding G proteins of *Caenorhabditis elegans,*" Nature Genetics, *21(4)*: 414–419 (1999).

Fire, et al., "A modular set of *lacZ* fusion vectors for studying gene expression in *Caenorhabditis Elegans* (Recombinant DNA; nematode; β–galactosidase; nuclear localization; transmembrane; expression vector; heat shock; transgenic animals)," *Gene, 93(2)*: 189–198 (1990).

* cited by examiner

*Primary Examiner*—Peter Paras, Jr.
(74) *Attorney, Agent, or Firm*—Elizabeth Hecht; Edward R. Gimmi; Charles M. Kinzig

(57) ABSTRACT

This invention relates to methods for producing a transgenic *C. elegans* that expresses a human 7TMR pan-neuronally, such that said transgenic *C. elegans* exhibits a known phenotype. These transgenic *C. elegans* can be used in a variety of ways, including, but not limited to: (1) screening and identifying substances that bind to and activate particular human 7TMRs; (2) screening for substances that antagonize human 7TMR activation; (3) identifying human 7TMRs that may respond to particular substances; and (4) evaluating the specificity and efficacy of substances on human 7TMR activation.

10 Claims, 5 Drawing Sheets

CAENORHABDITIS ELEGANS CHEMOSENSORY BIOASSAY FOR SEVEN TRANSMEMBRANE RECEPTOR LIGANDS

CROSS-REFERENCE TO RELATED APPLICATION

This application claims benefit to the earlier provisional U.S. application Ser. No. 60/237,290, filed on Oct. 2, 2000, the contents of which are incorporated herein by reference in their entirety.

FIELD OF THE INVENTION

This invention relates to methods for producing a transgenic *Caenorhabditis elegans* (*C. elegans*) that expresses a human 7-transmembrane receptor (herein "7TMR") in its neurons that correlate with behavior. These transgenic *C. elegans* nematodes can be used in a variety of ways, including, but not limited to: (1) screening and identifying substances that bind to and activate human 7TMRs; (2) screening for substances that antagonize human 7TMRs; (3) identifying 7TMRs that may respond to particular substances; and (4) evaluating the specificity and efficacy of substances on human 7TMR activation.

BACKGROUND OF THE INVENTION

With the increasing flow of DNA sequence information from a variety of species, including humans, there is a need for new methods that can link function with gene sequence. We have developed an invention useful for probing the function of cell surface, transmembrane receptors, including the largest, and most pharmacologically important, gene classes in multicellular organisms, the seven transmembrane receptor (herein referred to as "7TMR") class of genes. See generally Stadel, et al., *Trends Pharmacol. Sci.* 18(11): 430–7 (1997). Receptors often reside at the membrane surface of the cell and, upon binding of a ligand, activate an intracellular signaling cascade that mediates a particular cellular response. A crucial step in understanding the function of a particular receptor is to identify the ligand, or a surrogate ligand, that can bind and activate the receptor. The invention we describe here, which we dub the "*C. elegans* Chemosensory Bioassay," allows nematodes to sense and respond to substances that may affect cell surface receptor activity. This invention can be used in a variety of ways, including, but not limited to: (1) screening and identifying substances that bind to and activate human 7TMRs; (2) screening for substances that antagonize human 7TMR activation; (3) identifying human 7TMRs that may respond to particular substances; and (4) evaluating the specificity and efficacy of substances on human 7TMR activation.

The instant invention represents a significant improvement over current technologies for probing transmembrane receptor function. Current methods for identifying activating for receptors are, at best, medium throughput (See Stadel, et al., supra.). Elaborate and sophisticated molecular assays designed to measure such parameters as calcium mobilization, cAMP, GTP-γ S binding, inositol phosphate production, MAP kinase activation, etc., are used to identify activating substances. These assays involve either sophisticated machines that can detect receptor activation in transgenic mammalian cell lines (Sullivan, et al., *Methods Mol Biol* 114:125–33 (1999)) or labor-intensive methods, such as microinjection of *Xenopus* oocytes followed by electrophysiological recording (Wagner, et al., *Cell Physiol Biochem.* 10(1–2): 1–12 (2000)) Such assays involve direct mechanical detection of receptor function.

By contrast, our invention links receptor activation to simple nematode behaviors, obviating the need for sophisticated instrumentation. In addition, the self-replicating biological nature of nematodes allows large numbers of animals to be produced in the laboratory, ensuring that our invention will be an inexpensive solution and will be amenable to high-throughput applications. For example, libraries of substances can be easily screened, as discussed below. Also, unlike mechanical detection of receptor activation, our invention does not require any prior assumptions about the parameters to be measured (calcium, cAMP, etc.). Instead, our invention uses simple biological behaviors in nematodes to assay receptor activation.

Cell surface receptors are a large collection of proteins that fit into a number of superfamilies by their structural similarities. These superfamilies include, but are not limited to: ion channels, transporters, and 7 transmembrane receptors (Saier M H Jr, *J Membr Biol* 175(3):165–180 (2000); Saier M H Jr, *J Cell Biochem,* Suppl 32–33:84–94 (1999); Bockaert J, Pin J P, *EMBO* 18(7): 1723–1729 (1999)). It is well established that many medically significant biological processes are mediated by such proteins. For example, the most common inherited disease among caucasians is cystic fibrosis, caused by mutations in the CFTR chloride channel (Frizzell R A *Physiol Rev,* 79(1 Suppl): S1–2 (1999)). In addition, a number of other disease states are linked to mutations in other ion channels (Weinreich F, Jentsch T J, *Curr Opin Neurobiol* 10(3):409–415 (2000)). One role of the transporter class of cell surface proteins is the uptake of neurotransmitters from synaptic clefts in the nervous system. These transporters are targets for therapeutic intervention in a variety of psychiatric disorders. For example, selective serotonin uptake inhibitors are used in the treatment of a number of disorders and include the widely prescribed drug Prozac (Masand P S, Gupta S, *Harv Rev Psychiatry,* 7(2):69–84 (1999)).

Among the cell surface receptor superfamilies, the 7 transmembrane receptor (7TMR) superfamily appears to be the largest in metazoan organisms (see Bockaert and Pin, supra). 7TMRs mediate a variety of cellular responses to extracellular stimuli. For example, 7TMRs bind or interact with a huge variety of ligands; including photons, small molecules, and large proteins (see Bockaert and Pin, supra). 7TMRs are be intracellularly coupled by heterotrimeric G-proteins to various intracellular enzymes, ion channels and transporters (see, Johnson, et al., *Endoc. Rev.,* 1989, 10:317–331). The 7TMRs include dopamine receptors, which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors. Thus, these receptors mediate a large variety of biological and cellular responses to extracellular cues and include a wide range of biologically active receptors, such as hormone, viral, growth factor and neuroreceptors.

For most cell surface receptors identified in genome sequencing efforts, the activating ligand is not known. However, given the wide variety and important nature of biological processes regulated by cell surface receptors, determination of the activating ligand is of fundamental pharmaceutical importance. For example, over the past 15 years nearly 350 therapeutic agents targeting 7TMRs have been successfully introduced onto the market (See Stadel, et al., supra). Therefore, finding out what ligands bind these 7TMRs will enable researchers to develop drugs to either agonize or antagonize the interaction of 7TMRs with their ligands. Our invention can be applied to this problem and is useful for probing the function of a large number of cell surface protein types by linking simple *C. elegans* behaviors to the activation of human 7TMRs.

SUMMARY OF THE INVENTION

In one aspect, the invention relates to a method for producing a transgenic *Caenorhabditis elegans* (*C. elegans*) that expresses at least one human 7TMR pan-neuronally, such that said transgenic *C. elegans* exhibits a known phenotype, said method comprising the steps of:

(a) producing a transgene by operably linking a gene expression construct that encodes a human 7TMR to a pan-neuronal promoter; and (b) introducing said transgene into said transgenic *C. elegans*, such that said transgenic *C. elegans* expresses said human 7TMR pan-neuronally; and (c) examining said *C. elegans* to determine that said *C. elegans* exhibits a known phenotype.

During the practice of this method, wherein the known phenotype is selected from the group consisting of: exploded (Exp), dumpy (Dpy), long body (Lon), hyperactive movement (Hpr), paralyzed (Prl), molt defect (Mlt), sterile (Ste), sick (Sck), body morphology defect (Bmd), vulvaless (Vul), slow growth (Gro), egg laying defect (Egl), larval arrest (Lva), protruding vulva (Pvl), multiple vulva (Muv), sterile progeny (Stp), small (Sma), clear (Clr), blistered (Bli), high incidence of male progeny (Him), roller (Rol), larval lethal (Lvl), uncoordinated (Unc), embryonic lethal (Emb).

In another aspect, this invention provides a transgenic *C. elegans* produced by the above method.

In one aspect, the invention relates to a method for producing a transgenic *Caenorhabditis elegans* that expresses a human 7-transmembrane receptor (7TMR) in the sensory neurons that correlate with behavior, said method comprising the steps of:

(a) producing a transgene by operably linking a gene expression construct that encodes a human 7TMR to a sensory neuron promoter; and (b) introducing said transgene into said *C. elegans*, such that said *C. elegans* expresses said human 7TMR in its sensory neurons that correlate with behavior.

The gene expression construct used in this method can be either DNA or a plasmid. The behavior referred to in this method is selected from the group consisting of: water-soluble chemorepulsion, water-soluble chemoattraction, volatile chemorepulsion, volatile chemoattraction, thermorepulsion, thermoattraction, and dauer formation.

In one aspect of this method, the behavior is water-soluble chemorepulsion, and said sensory neurons are selected from the group consisting of: ASH and ADL neurons. In this method, the sensory neuron promotor is the promotor region of gpa-11, and the plasmid construct is pCEASH2.1.

In another aspect, the instant invention relates to the above-referenced method, wherein said behavior is water-soluble chemoattraction, and said sensory neurons are selected from the group consisting of: ASE, ADF, ASG, and ASI neurons. In this method, the sensory neuron promotor is the promotor region of a gene selected from the group consisting of: gcy-5, gcy-6, and gcy-7.

In yet another aspect of this method, the behavior is volatile chemorepulsion, and said sensory neurons are AWB neurons. In this embodiment of the invention, the sensory neuron promoter is the promotor region of str-1.

In another aspect of this method, the behavior is volatile chemoattraction, and the sensory neurons are AWA neurons. In this embodiment, the sensory neuron promotor is the promotor region of odr-10.

In another aspect of this method, the behavior is dauer formation, and said sensory neurons are selected from the group consisting of: ASI, ASG, and ADF neurons.

In yet another aspect of this method, the behavior is selected from the group consisting of: thermoattraction and thermorepulsion, and said sensory neurons are AFD neurons. In this embodiment, the sensory neuron promoter is the promotor region of gcy-8.

In another aspect, this method of producing transgenic *C. elegans* further comprises the step of:

(c) introducing a DNA construct that expresses a reporter gene with a nematode promotor.

Preferably, this reporter gene encodes a fluorescent protein, such as a green fluorescent protein (GFP).

In another aspect, this invention provide a method for producing a transgenic *C. elegans* that expresses a human 7TMR receptor in the sensory neurons that correlate with behavior, said method comprising the steps of:

(a) producing a first transgene by operably linking a gene expression construct that encodes a human 7TMR to a sensory neuron promotor;

(b) producing a second transgene by comprising an accessory protein operably linked to a promotor; and (c) introducing said first and second transgenes into said *C. elegans*, such that said *C. elegans* coexpresses both said accessory protein and said human 7TMR in its sensory neurons that correlate with behavior.

In one embodiment of this method, the non-nematode cell surface receptor is a 7TMR, and said accessory protein is a human G protein.

Another embodiment of this invention encompasses a transgenic *C. elegans* produced by any of the above-described methods.

In yet another aspect, this invention provides a method for identifying at least one ligand of at least one human 7TMR, said method comprising the steps of:

(a) providing at least one *C. elegans* that expresses at least one human 7TMR in the sensory neurons that correlate with behavior;

(b) contacting said at least one *C. elegans* with at least one test substance; and (c) detecting modulation of behavior of said at least one *C. elegans* in response to said at least one test substance.

In this screening method, the behavior is selected from the group consisting of: water-soluble chemorepulsion, water-soluble chemoattraction, volatile chemorepulsion, volatile chemoattraction, thermorepulsion, thermoattraction, and dauer formation.

In another aspect, the instant invention provides a method for identifying at least one ligand of at least one human 7TMR, said method comprising the steps of:

(a) providing at least one *C. elegans* that expresses at least one 7TMR in its sensory neurons that correlate with water-soluble chemorepulsive behavior;

(b) placing a medium into a first portion of a receptacle, wherein said receptacle is divided into at least two portions;

(c) adding at least two different concentrations of at least one chemorepulsant substance to the first portion of said receptacle;

(d) adding said at least one *C. elegans* to the second portion of said receptacle; and (e) detecting, after a suitable time period, the behavioral response of said at least one *C. elegans* to said at least one chemorepulsant substance.

In yet another aspect, this screening method further comprises the following step:

(f) generating a chemotactic index, wherein said chemotactic index is the fraction of said at least one *C. elegans* that moved to said first portion of said receptacle.

In another aspect of this method, said sensory neurons are selected from the group consisting of: ASE, ADF, ASG and ASI neurons.

In this method, said at least one chemorepulsive substance is selected from the group consisting of: copper sulfate, sodium dodecyl sulfate (SDS), D-tryptophan, heptanol, octanol, nonanol, nonanone, benzaldehyde, 2,4,5-trimethylthiazole, and ethyl heptanoate.

In one embodiment of this screening method, the growth medium comprises a biomolecular separation in a matrix. This matrix is selected from the group consisting of: agarose and polyacrylamide.

In one aspect of this screening method, said at least one test substance can is present in beads on a solid or semi-solid medium.

In other aspects of this screening method, said at least one test substance comprises at least one natural peptide, a viral plaque, or is secreted by at least one miroorganismal colony. In another aspect, said at least one test substance is a recombinant peptide that is secreted by at least one microorganismal colony. Said at least one recombinant peptide can be a peptide library. Said microorganismal colony is selected from the group consisting of: bacteria and yeast.

In yet another aspect of this screening method, said detecting step (e) is carried out by direct detection with a suitable optical instrument. Said detecting step (e) can carried out by assisted detection of the optical density over the surface of said medium. Alternatively, said assisted detection can be mechanical detection.

In a yet another aspect, the instant invention provides a method for identifying at least one ligand of at least one human 7TMR, said method comprising the steps of:

(a) providing at least one *C. elegans* that expresses at least one human 7TMR in its sensory neurons that mediate water-soluble chemoattractive behavior;

(b) placing a medium into a first portion of a receptacle, wherein said receptacle is divided into at least two portions;

(c) adding at least two different concentrations of at least one chemoattractant substance to the first portion of said receptacle;

(d) adding said at least one *C. elegans* to the second portion of said receptacle; and (e) detecting, after a suitable time period, the behavioral response of said at least one *C. elegans* to said at least one chemoattractant substance.

In another aspect of this method, said sensory neurons are selected from the group consisting of: ASE, ADF, ASG and ASI neurons.

In yet another aspect of this invention, this method further comprises the following step:

(f) generating a chemotactic index, wherein said chemotactic index is the fraction of said at least one *C. elegans* that moved to said first portion of said receptacle.

In one embodiment of the instant invention, said at least one chemoattractant substance is selected from the group consisting of: isoamyl alcohol, biotin, lysine, histidine, cysteine, and serotonin.

In another aspect, this invention provides a method for identifying at least one ligand of a human 7TMR said method comprising the steps of:

(a) providing at least one *C. elegans* that expresses a human 7TMR in the sensory neurons that correlate with behavior;

(b) placing at least one test substance on a substrate surface that contains growth medium;

(c) placing a uniform lawn of bacteria onto the surface of said growth medium;

(d) contacting said at least one *C. elegans* with the surface of said growth medium; and (e) detecting, after a suitable time period, a decrease in the density of said uniform lawn of bacteria.

The bacteria employed in this method is selected from the group consisting of: *Acinetobacter calcoaceticus, Bacillus cereus, Bacillus* sp., *Enterobacter amnigenus, Enterohacter cloacae, Escherichia coli, Flavohacterium* sp., *Proteus vulgaris, Pseudomonas aeruginosa, Pseudomonas cepacia, Pseudomonas maltophilia, Pseudomonas putida, Pseudomonas* sp., *Serratia liquefaciens, Serratia marcesens, Zymobacillus macerans*. Preferably, the bacteria used in this method is *E. coli*.

In yet another aspect of this method, the detection step (e) comprises photometrically determining variations in the density of said bacterial lawn.

In a further aspect of this screening method, the bacteria express GFP, and the detecting step (e) comprises determining the fluorescence intensity of said bacterial lawn.

In yet another aspect, the instant invention provides a method for identifying at least one ligand of at least one human 7TMR, said method comprising the steps of:

(a) providing at least one *C. elegans* that expresses a human 7TMR in the sensory neurons that correlate with behavior;

(b) placing a medium in a receptacle;

(c) arranging at least one test substance in said receptacle;

(d) adding said at least one *C. elegans* to said receptacle; and (e) detecting, after a suitable time period, the behavioral response of said at least one *C. elegans* over the surface of said medium.

In another aspect, the instant invention provides a method for evaluating the potency of human 7TMR activation by a known ligand, said method comprising the steps of:

(a) providing at least one *C. elegans* that expresses at least one human 7TMR in the sensory neurons that correlate with behavior, wherein said at least one human 7TMR has a known ligand;

(b) contacting said at least one *C. elegans* with said ligand and at least one structurally related compound; and (c) detecting the behavioral response of said at least one *C. elegans* to said at least one structurally related compound; and (d) comparing the behavioral response of said at least one *C. elegans* to said ligand to the behavioral response of said at least one *C. elegans* to said at least one structurally related compound.

In one aspect of this method, the behavior is selected from the group consisting of: chemoattraction and chemorepulsion.

In another aspect, this invention relates to a method for identifying at least one test substance that modulates the activation of at least one human 7TMR by a known ligand, said method comprising the steps of:

(a) providing at least one C. elegans that expresses at least one human 7TMR in the sensory neurons that correlate with behavior, wherein said at least one human 7TMR has a known ligand;

(b) contacting said at least one C. elegans with at least one test substance in the presence of said known ligand; and (c) determining whether said at least one test compound binds to and activates or inhibits the activation of said at least one human 7MR by said ligand by measuring the alteration of behavior of said at least one C. elegans in response to said at least one test substance.

In a further aspect of this method, the behavior that is measured is selected from the group consisting of: water-soluble chemorepulsion, water-soluble chemoattraction, volatile chemorepulsion, volatile chemoattraction, thermorepulsion, thermoattraction, and dauer formation.

In yet another aspect, this invention provides a method for identifying at least one test substance that is an antagonist of a human 7TMR, said method comprising the steps of:

(a) providing at least one C. elegans that expresses a human 7TMR pan-neuronally, wherein said human 7TMR is activated by an endogenous ligand, such that said transgenic C. elegans exhibits a known phenotype;

(b) contacting said at least one C. elegans with at least one test substance, wherein said at least one test substance is distributed in a medium;

(c) determining whether said at least one test substance causes a suppression of said known phenotype in said at least one transgenic C. elegans; and (d) identifying said at least one test substance that causes a suppression of said known phenotype in said at least one transgenic C. elegans as an antagonist of said human 7TMR.

In another aspect, this invention provides a method for identifying a surrogate ligand present in a strain of transgenic C. elegans that expresses a human 7TMR pan-neuronally, wherein said strain of transgenic C. elegans exhibits a known phenotype, such that said human 7TMR is activated by an endogenous ligand, said method comprising the steps of:

(a) providing a strain of human 7TMR-expressing transgenic C. elegans, wherein said strain of transgenic C. elegans exhibits a known phenotype;

(b) subjecting said strain of transgenic C. elegans to at least one mutagenic screen; and (c) determining whether said at least one mutagenic screen results in a suppression of said known phenotype in said strain of transgenic C. elegans.

In yet another aspect, this invention provides a method for identifying at least one substance that agonize the activity of a human 7TMR, said method comprising the steps of:

(a) providing at least one transgenic C. elegans that expresses a human 7TMR pan-neuronally, wherein said at least one transgenic C. elegans does not exhibit a known phenotype because said human 7TMR is not activated by an endogenous ligand;

(b) contacting said at least one transgenic C. elegans with at least one test substance, wherein said at least one test substance is distributed in a medium;

(c) determining whether said at least one test substance causes said at least one said transgenic C. elegans to exhibit a known phenotype; and (d) identifying said at least one test substance that causes said at least one said transgenic C. elegans to exhibit a known phenotype as an agonist of said human 7TMR.

GLOSSARY

Figure 1:
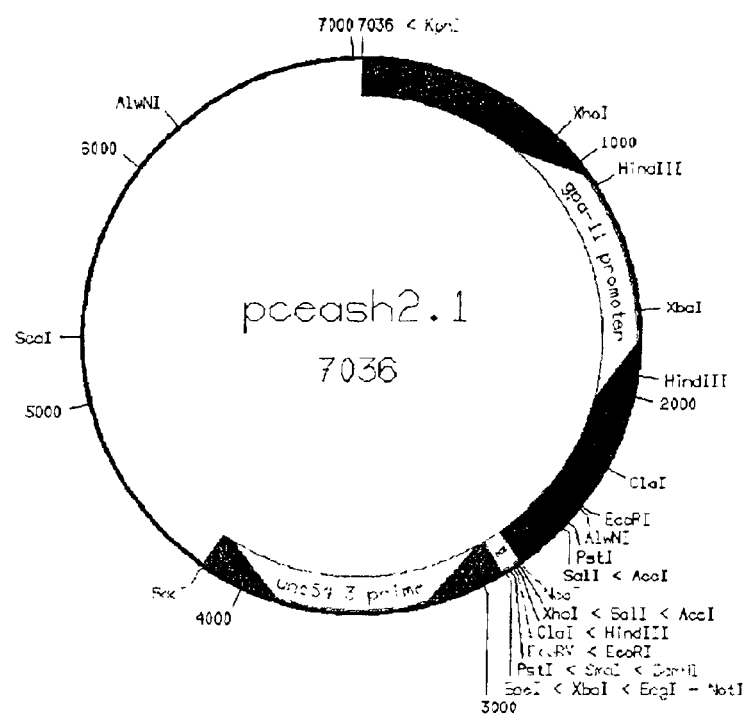
FIG. 1 diagrams the pCEASH2.1 plasmid, which is capable of driving expression in the ADL and ASH neurons of C. elegans that mediate water-soluble chemorepulsion. In brief, the promoter region of the gpa-11 gene has been placed in a plasmid context with the 3' region of the unc-54 gene (see example 1 text for a detailed description). This gpa-11 promoter region is sufficient to drive expression in the C. elegans ADL and ASH neurons.

The following illustrative explanations are provided to facilitate understanding of certain terms used frequently herein. The explanations are provided as a convenience and are not limiting of the invention.

The term, "behavior," as used herein, refers to behavior selected from the group consisting of: volatile chemotaxis, water-soluble chemotaxis, thermotaxis, and dauer formation. More specifically, these behaviors encompass water-soluble chemorepulsion, water-soluble chemoattraction, volatile chemorepulsion, volatile chemoattraction, thermorepulsion, and thermoattraction.

The term, "chemoattractant substance," as used herein, refers to both known chemoattractants, such as isoamyl alcohol, biotin, lysine, histidine, cysteine, and serotonin (Bargmann C I., *Chemotaxis and Thermotaxis,* In Riddle, Blumenthal, Meyer, and Priess (eds.), *C. ELEGANS* II, Cold Spring Harbor Laboratory Press, Cold Spring Harbor, N.Y. (1997)), as well as substances that are discovered to elicit chemoattractive behavior from transgenic *C. elegans* of the instant invention.

The term, "chemorepellant substance," as used herein, refers to both known chemorepellants, such as copper sulfate, sodium dodecyl sulfate (SDS), D-tryptophan, heptanol, octanol, nonanol, nonanone, benzaldehyde, 2,4,5-trimethylthiazole, and ethyl heptanoate (Bargmann, supa), as well as substances that are discovered to elicit chemorepulsive behavior from transgenic nematodes of the instant invention.

As used herein, phrase "known phenotype," includes, but is not limited to, the following phenotypes that have been scored in *C. elegans*: exploded (Exp), dumpy (Dpy), long body (Lon), hyperactive movement (Hpr), paralyzed (Prl), molt defect (Mlt), sterile (Ste), sick (Sck), body morphology defect (Bmd), vulvaless (Vul), slow growth (Gro), egg laying defect (Egl), larval arrest (Lva), larval lethal (Let), protruding vulva (Pvl), multiple vulva (Muv), sterile progeny (Stp), small (Sma), clear (Clr), blistered (Bli), high incidence of male progeny (Him), roller (Rol), larval lethal (Lvl), uncoordinated (Unc), embryonic lethal (Emb).

As used herein, the term, "operably linked," refers to a DNA sequence and a regulatory sequence(s) that are connected in such a way as to permit gene expression when the appropriate molecules, e.g., transcriptional activator proteins, are bound to the regulatory sequence(s). A nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

As used herein, the term, "pan-neronal" or "pan-neuronally" refers to the expression of a given gene in all of the neurons of a transgenic *C. elegans*.

The term, "structurally related compounds," as it is used herein, refers to compounds that share a common pharamacophore, which is a core structure of the compound that has biological activity. Such "structurally related compounds" can differ from each other, however, in their substituent groups. As used in the screening assays herein, "structurally related compounds" share a pharmacophore with a known or newly discovered ligand of a non-nematode cell surface receptor that is expressed in the transgenic nematodes described below.

The term, "test population," as it is used herein, refers to a group *C. elegans* from the same strain that each express the same human 7TMR(s).

The term, "test substance," as used herein, refers to an organic or inorganic molecule, a homogenous mixture of such molecules, biological extracts, or biological fractions. A "test substance" could be, for example, a viral plaque or a natural peptide. A "test substance" could be, for example, a known chemoattractant or chemorepulsant compound or a molecule that is discovered to elicit chemosensory behavior from transgenic nematodes of the instant invention.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, S. N., *Proc. Natl. Acad. Sci.* (*USA*), 69: 2110 (1972) and Mandel, et al., *J. Mol. Biol.* 53: 154 (1970), is generally used for prokaryotes or other cells that contain substantial cell-wall barriers. For mammalian cells without such cell walls, the calcium phosphate precipitation method of Graham, et al., *Virology* 52: 456–457 (1978) is preferred. General aspects of mammalian cell host system transformations have been described by Axel in U.S. Pat. No. 4,399,216, issued Aug. 16, 1983. Transformations into yeast are typically carried out according to the method of Van Solingen, P., et al., *J. Bacteriology* 130: 946 (1977) and Hsiao, C. L., et al. *Proc. Natl. Acad. Sci* (USA) 76: 3829 (1979). However, other methods for introducing DNA into cells such as by nuclear injection, electroporation or by protoplast fusion may also be used. Transformations into *C. elegans* can be carried out by microinjection, as described in Mello C C, et al, *EMBO J.* 10:3959–3970 (1991), or by microparticle bombardment as described in Wilm T, et al., *Gene* 229:31–35 (1999) and Praitis et al., *Genetics* 157, 1217–26 (2001).

DETAILED DESCRIPTION OF THE INVENTION

In a particularly preferred embodiment of the invention, the roundworm *Caenorhabditis elegans* is employed. *C. elegans* is a simple soil nematode species that has been extensively described at the cellular and molecular level, and is a model organism for biological studies (See Riddle, *C. ELEGANS* II., Cold Spring Harbor Laboratory Press, Cold Spring Harbor, N.Y. (1997); The *C. elegans* Sequencing Consortium, *Science* 282: 2012–2018. (1998); Sulston, W B (ed), THE NEMATODE *CAENORHABDITIS ELEGANS,* Cold Spring Harbor Laboratory Press, Cold Spring Harbor, N.Y., pp. 123–155 (1988)). The adult hermaphrodite is composed of 959 cells, 302 of which are defined as neuronal cells. Sulston, supra. *C. elegans* can respond to a variety of substances in its environment by moving away from a point source, termed chemorepulsion, or moving toward a point source, termed chemoattraction. Bargmann, supra. *C. elegans* also responds to a pheromone in the environment by taking an alternative developmental pathway, the dauer stage. Riddle, et al., *Genetic and Environmental Regulation of Dauer Larva Development,* In Riddle, Blumenthal, Meyer, and Priess (eds), *C. ELEGANS* II., Cold Spring Harbor Laboratory Press, Cold Spring Harbor, N.Y. (1997). Much of this chemosensory behavior is mediated by sensory organs termed the amphids, a pair of bilaterally symmetric structures located at the anterior of the animal. Each amphid contains the endings of 12 sensory neurons, eight of which are directly exposed to the environment through an opening in the cuticle of the animal. Bargmann, supra. The cell bodies of the sensory neurons lie in the nerve ring of the animal, where they synapse with other neurons to pass on sensory information. The function of each amphid sensory neuron has been defined by laser ablation microsurgery and subsequent testing of the operated animal. Id. Each type of sensory modulates a particular chemosensory behavior. For example, the AWA neuron mediates chemotaxis toward volatile compounds, including diacetyl, pyrazine, and thiazole; whereas the AWB neuron mediates chemorepulsive behavior toward volatile compounds. The ASI, ASG, and ADF neurons are necessary in the process of dauer pathway commitment. Riddle, et al., supra. The AFD neurons mediate thermotaxic behavior, which includes thermoattraction and thermorepulsion. Bargmann, supra. The observation that particular neurons are needed for different behaviors suggests that behavioral modalities are determined by the properties and synaptic connections of these neurons.

While chemotactic behavior is determined at the neuronal level, the ability to discriminate among substances in the environment is determined by expression of particular receptors in the chemosensory neurons. For example, a C. elegans 7TM receptor, odr-10, has been defined as a requisite receptor for the chemotactic response of C. elegans to diacetyl. Sengupta, et al., Cell 84: 899–909 (1996). Animals that are mutant for the odr-10 gene no longer respond to diacetyl, and expression of odr-10 in mammalian tissue culture cells confers Ca+2 mobilization in response to diacetyl, indicative of activation. Sengupta, et al., supra; Zhang, et al., PNAS, USA 94: 12162–67 (1997). In C. elegans, ODR-10 is normally expressed in the AWA neuron, which mediates chemoattraction to diacetyl. These results strongly indicate that the ligand for odr-10 is diacetyl, and ligand binding and odr-10 activation in the AWA neuron leads to a chemotactic response to diacetyl. Odr-10 belongs to a large family of 7TM receptors encoded in the genome of C. elegans, and it is likely that expression of these receptors in the sensory neurons provides the wide range of chemotactic chemical sensitivity seen in C. elegans. Given that different neurons are involved in different chemotactic behaviors, the expression of a receptor in certain neurons likely determines the behavioral response to the substance recognized by the receptor. Researchers tested this hypothesis by misexpressing odr-10 in the AWB neuron, which mediates volatile chemorepulsive behavior. Troemel, et al., Cell 91:161–169 (1997). This misexpression of odr-10 led to a "reprogramming" of the chemotactic response, such that the animals showed chemorepulsive behavior to diacetyl, instead of chemoattraction. These observations lead us to believe that ligand specificity is provided by the receptor itself, while the behavioral response is determined by which neuron the receptor is expressed in.

The ability to reprogram the chemosensory response of C. elegans is not limited to misexpressing C. elegans receptors. At a recent C. elegans worm, a second example of reprogramming the chemosensory response of C. elegans was presented using a mammalian-derived receptor. Summary of Tobin. et al., Neuron 35: 307–318 (2002). Expression of the mammalian capcaicin receptor VR1 in sensory neurons of C. elegans conferred a chemoavoidance behavior in response to capsaicin. Like the odr-10 example discussed above, this report is a demonstration that nematode chemosensory behavior in response to substances can be modified by expression of a receptor in the sensory neurons of nematodes. Unlike our invention, the authors do not express the human capsaicin receptor in C. elegans with the purpose of using chemotactic behavior as a way of identifying substances that activate the receptor, nor do they propose that such an application is possible. We propose that the modification of chemosensory behavior by human 7TMR expression in sensory neurons can be applied to the identification and characterization of substances that activate human 7TMRs or modify human 7TMR activity.

Production of Transgenic C. elegans

The transgenic C. elegans of this invention can be used in a variety of ways, including, but not limited to: (1) screening and identifying substances that bind to and activate particular human 7TMRs; (2) screening for substances that antagonize human 7TMR activation; (3) identifying human 7TMRs that may respond to particular substances; and (4) evaluating the specificity and efficacy of substances on human 7TMR activation.

One preferred embodiment of the invention includes a method for producing a transgenic C. elegans that expresses a human 7TMR in the sensory neurons that correlate with behavior, said method comprising the steps of:

(a) producing a transgene by operably linking a gene expression construct that encodes a human 7TMR to a sensory neuron promotor; and (b) introducing said transgene into said C. elegans, such that said C. elegans expresses said human 7TMR in the sensory neurons that correlate with behavior.

In one particularly preferred embodiment of the instant invention, transgenic C. elegans are used as biosensors for substances that activate human 7TMRs or that block human 7TMR activation. This is accomplished by specific expression of human 7TMR(s) in the appropriate sensory neurons of C. elegans, allowing the organisms to sense and respond in a chemosensory fashion to substances that activate the human 7TMR(s). By expressing human 7TMR(s) in particular sensory neurons, the response of the animals to receptor activation will be manifested as one of several behaviors: chemorepulsion, chemoattraction, thermotaxis, including thermoattraction and thermorepulsion, or commitment to the dauer developmental pathway. Chemorepulsion can be toward volatile compounds, mediated by the AWB sensory neuron of C. elegans, or toward water-soluble compounds, mediated by the ASH and ADL sensory neurons. A human 7TMR can be expressed in the AWB neuron of C. elegans using the promoter region of the str-1 gene operably linked to the receptor coding sequence (Troemel E R, et al, Cell 91:161–169 (1997)). A receptor can be expressed in the ASH and ADL neurons using the promoter region of the gpa-11 gene operably linked to the receptor coding sequence (Jansen G, et al, Nature Genetics 21:414–419 (1999)). Chemoattraction can likewise by toward volatile compounds, mediated by the AWA neuron, or toward water-soluble compounds, mediated by the ASE, ADF, ASG, and ASI neurons. A receptor can be expressed in AWA using the promoter region of the odr-10 gene operably linked to the receptor coding region (Troemel E R, et al, supra). A receptor can be expressed in the ASE neuron using the promoter regions of the gcy-5, gcy-6, or gcy-7 genes operably linked to the receptor coding region (Yu S, et al, PNAS 91:3384–3387 (1997)). Dauer formation is mediated by the ADF, ASI and ASJ neurons; a human 7TMR can be expressed in these neurons using the promoter region of the gpa-10 gene operably linked to the receptor coding region (Jansen G, et al, supra). Thermotaxis is mediated by the AFD neuron; a human 7TMR can be expressed in this neuron using the promoter of the gcy-8 gene operably linked to the receptor coding region (Yu S, et al, supra). Once a human 7TMR is expressed in the appropriate neuron to elicit a desired behavior, these behaviors can then be used to, for example, identify the substances that act as ligands to activate the human 7TMR, identify substances that antagonize the human 7TMR activation, determine the human 7TMR that is activated by a particular substance, or determine the potency and efficacy of activating substances.

In a particularly preferred embodiment of the invention, transgenic *C. elegans* are produced that express human 7TMRs in the sensory neurons that correlate with behavior, as discussed above. Such human 7TMRs are expressed in particular sensory neurons of in the transgenic *C. elegans* to select the desired behavior of the transgenic *C. elegans* upon human 7TMR activation. DNA constructs that direct expression of human 7TMRs will be composed of up to four different DNA segments: (1) a promoter segment; (2) an optional signal peptide encoding segment; (3) a receptor-encoding segment; and (4) and a 3' segment. These constructs are then introduced into nematodes by methods well known in the art to produce a stable strain that express the receptors in the appropriate sensory neurons.

The promoter DNA segment, importantly, confers the appropriate temporal and spatial characteristics to human 7TMR expression. In *C. elegans*, chemotactic behavior can be defined in four broad categories, each mediated by a subset of sensory neurons. Bargmann, supra. Genes that are expressed in particular sets of sensory neurons are known. Using recombinant DNA technique, the promoters or DNA segments that confer temporal/spatial specificity to these genes can be fused to a heterologous gene. Sambrook, et al., 1. *Plasmid Vectors*. In Sambrook J, Fritsch E F, and Maniatis, T (eds), MOLECULAR CLONING: A LABORATORY MANUAL, Cold Spring Harbor Laboratory Press, Cold Spring Harbor, N.Y. (1989).

For example, reporter gene expression in the ADL and ASH neurons, both of which mediate avoidance behavior when exposed to water-soluble substances, can be driven by the gpa-11 promoter. Jansen, et al., *Nature Genetics* 21: 414–419 (1999). Any such promoter or DNA regulatory element is suitable, provided it directs gene expression specifically, and solely, in sensory neurons that mediate a particular behavior. The promoter segment should include all necessary DNA to provide transcriptional initiation, 5' mRNA processing, and translational initiation at a methionine start codon.

In order to bind exogenously applied substances, human 7TMRs are, preferably, localized to the cell surface membrane of the expressing cells. Proteins can be directed to the cell surface by virtue of a signal peptide sequence that is found at the amino-terminal portion of the protein. Heijne, *Nucleic Acids Research* 14: 4683–4690 (1986). This signal peptide sequence can be introduced in one of two ways. First, the DNA segment encoding the receptor itself may already include a functional signal peptide sequence. Thus, directing the human 7TMR to the cell surface, where it can respond to extracellular molecules, can be accomplished by maintaining the peptide signal sequence of an inserted receptor protein coding sequence. Alternatively, a separate DNA segment that encodes a peptide signal sequence can be introduced between the promoter and receptor-encoding DNA.

Ideally, the receptor-encoding segment of DNA will include the nucleotides necessary to encode the complete human 7TMR peptide, from the start methionine codon to the translational termination, or stop, codon. The DNA segment should be operably linked to the promoter DNA segment such that translational initiation will begin at the start methionine codon of the receptor-encoding DNA segment.

A 3' DNA segment is necessary to provide the appropriate transcriptional termination and 3' mRNA processing signals. Although the 3' regions of many genes may be sufficient for this purpose, the standard DNA segment used for expression in *C. elegans* is composed of a 3' portion of the unc-54 gene. Fire, et al., *Gene* 93:189–198 (1990). See Example 1, which depicts how to create a DNA construct that is capable of driving expression of a non-nematode cell surface receptor in the ADL and ASH neurons of *C. elegans* that mediate water-soluble chemorepulsion. Other vectors have been described that can drive expression in the AWA and AWB neurons (Troemel E R, et al, *Cell* 91:161–169 (1997)).

Plasmid constructs can be introduced into *C. elegans* using described transformation methods to generate animals transgenic for the plasmid constructs. Mello, et al., *EMBO J*. 10: 3959–3970 (1991). Preferably, the plasmid used for this method is a linear plasmid. An important aspect of transformation in *C. elegans* is that plasmid constructs are easily cotransformed. Mello, et al., supra. Therefore, transgenic strains of *C. elegans* can be generated that express more than one human 7TMR. In addition, dominant cotransformation markers can be used to score for transgenic *C. elegans*. In a particularly preferred embodiment of the invention, a cotransformation marker that does not affect the ability of the animals to exhibit chemotactic behavior is used. This cotransformation marker can be, for instance, a DNA fragment that complements a mutant phenotype. For example, mutations in the *C. elegans* unc-119 gene cause a severe movement defect. Introduction of a segment of DNA containing the wildtype copy of the unc-119 gene will complement the movement defect (Maduro, *Genetics* 141: 977–88 (1995)), causing the transgenic animals to be wildtype in movement. Cotransforming unc-119 animals with the unc-119 wildtype DNA and the sensory neuron expression plasmids will allow the presence of the transgene to be scored by rescue of the unc-119 mutant phenotype. Alternatively, a reporter gene can be used that can be scored in a living animal, but does not affect the movement of the animal. For example, green fluorescent protein (herein referred to as "GFP") is a widely used reporter molecule in living systems. Ellenberg, *Trends Cell Biol*. 9(2): 52–56 (1999); Chalfie, et al., *Science* 263(5148): 802–05 (1994). Co-inject GFP-expressing DNA construct with the sensory neuron expression plasmids would allow the scoring for the presence of the transgene by examination of animals for GFP fluorescence. Ellenberg, et al., supra.

Therefore, in another aspect, this method of producing transgenic *C. elegans* further comprises the step of:

(c) introducing a DNA construct that expresses a reporter gene with a nematode promotor.

Preferably, this reporter gene encodes a fluorescent protein, such as a green fluorescent protein (GFP).

Expression and activation of a particular human 7TMR may not be sufficient to produce a behavioral response from a transgenic *C. elegans*. This may happen if the receptor requires accessory proteins to activate downstream signaling pathways. For example, many human 7TMRs activate downstream pathways through the action of heterotrimeric G proteins. Stadel, et al., supra. Although *C. elegans* contains 20 Gα, 2 Gβ, and 2Gγ G proteins (Jansen, et al., supra.), efficient activation of signaling pathways and subsequent behavioral response of the animal may require the coexpression of accessory proteins, such as G proteins. In a preferred embodiment of the invention, such accessory proteins are human G proteins. This can be accomplished using the same DNA constructs used to express the human 7TMR, replacing the receptor-encoding DNA segment with a DNA segment encoding the accessory protein. The constructs encoding the receptor and the accessory protein can then be cotransformed into nematodes.

A preferred embodiment of the invention provides a method for producing a transgenic *C. elegans* that expresses a human 7TMR in the sensory neurons that correlate with behavior, said method comprising the steps of:

(a) producing a first transgene by operably linking a gene expression construct that encodes a human 7TMR to a sensory neuron promoter;

(b) producing a second transgene by comprising an accessory protein operably linked to a promotor; and (c) introducing said first and second transgenes into said *C. elegans*, such that said *C. elegans* coexpresses both said accessory protein and said human 7TMR in the sensory neurons that correlate with behavior.

In a particularly preferred embodiment of this method, the accessory protein is a human G protein.

A preferred embodiment of the instant invention encompasses the transgenic *C. elegans* that are produced by the methods described above.

Assaying Behavior in Transgenic *C. elegans*

Test populations of transgenic *C. elegans* that express human 7TMRs in their sensory neurons will be able to sense and react to molecules or substances that modify receptor activity. Depending on the sensory neuron(s) that the human 7TMR(s) are expressed in, the reaction may be movement toward, or movement away from, a source of the substance; thermotaxis behavior; or commitment to the dauer pathway. A large variety of assays can be configured based on these behaviors. We first describe ways of presenting test substances to the animals, and then describe ways of measuring the behavior of the animals.

In one embodiment, the instant invention provides a method for identifying at least one ligand of at least one human 7TMR, said method comprising the steps of:

(a) providing at least one *C. elegans* that expresses at least one human 7TMR in the sensory neurons that correlate with behavior;

(b) contacting said at least one *C. elegans* with at least two different concentrations of at least one test substance; and (c) detecting modulation of behavior of said at least one *C. elegans* in response to said at least one test substance.

In a preferred embodiment of the invention, substances are presented to test populations of transgenic *C. elegans* in such a way that allows chemosensory behavior. In such chemotaxis assays, preferably, the animals are placed on a substrate that allows free movement, such as a solid or a semi-solid substrate. For example, a typical culture medium for *C. elegans* is composed of a buffered solidified agar substrate placed in a container such as a petri plate. Sulston W B, supra. The substrate medium can be buffer or it can be growth medium, such as agar. In order to observe chemotactic behavior, it is preferable that a test substance be present in at least two different concentrations at spatially distinct regions of the substrate. A number of standard chemotactic assays have been described, including assays that use point sources, gradients, and simple two concentration presentation of test substances. See Bargmann, supra; Troemel, et al., supra; Jansen, et al., supra. All of these assays have the following two characteristics: (1) a substrate medium allows the animals to locomote efficiently between, and show a preference for, different regions of the substrate; and (2) the presence of a test substance at two concentrations or more in spatially distinct regions of the substrate medium.

Test substances can be presented in a dispersed format, or a point source format. An example of a dispersed format presentation method is the water-soluble chemorepulsive assay that is performed in divided petri dishes. Jansen, et al, supra. In this format, a test substance is added to the agar poured in one half of a divided petri dish. In the other half of the petri dish, agar without the substance is poured. A small drop of isoamyl alcohol, which is a strong diffusable chemoattractant to *C. elegans*, is placed on the agar half that contains the test substance and a population of test animals is placed on the opposite half. Other known chemoattractants can be used, such as biotin, lysine, histidine, cysteine, and serotonin in place of the isoamyl alcohol. Bargmann, et al., supra. After a suitable time period, typically 90 minutes, the dispersion of animals on each half of the plate is quantitated by one of the methods discussed above. The fraction of animals that remain on the non-substance containing agar half of the petri plate is a reflection of how well the test substance can "repel" the animals. In assays with strong chemorepellants, such as copper sulfate, sodium dodecyl sulfate (SDS), D-tryptophan, heptanol, octanol, nonanol, nonanone, benzaldehyde, 2,4,5-trimethylthiazole, and ethyl heptanoate, more than 90% of the animals typically remain on the half of the agar plate without the chemorepellant. Jansen, et al, supra.; Bargmann, et al., supra. The chemorepulsive assay could be used in conjunction with the pCEASH2.1 vector described in example 1, which directs expression in sensory neurons that mediate water-soluble chemorepulsion.

In a particularly preferred embodiment, the instant invention provides a method for identifying at least one ligand of at least one human 7TMR, said method comprising the steps of:

(a) providing at least one *C. elegans* that expresses at least one human 7TMR in the sensory neurons that correlate with water-soluble chemorepulsive behavior;

(b) placing a medium into a first portion of a receptacle, wherein said receptacle is divided into at least two portions;

(c) adding at least two different concentrations of at least one chemorepulsant substance to the first portion of said receptacle;

(d) adding said at least one *C. elegans* to said second portion of said receptacle; and (e) detecting, after a suitable time period, the behavioral response of said at least one *C. elegans* to said at least one chemorepulsant substance.

In yet another particularly preferred embodiment, the instant invention provides a method for identifying at least one ligand of at least one human 7TMR, said method comprising the steps of:

(a) providing at least one *C. elegans* that expresses at least one human 7TMR in the sensory neurons that mediate water-soluble chemoattractive behavior;

(b) placing a medium into a first portion of a receptacle, wherein said receptacle is divided into at least two portions;

(c) adding at least two different concentrations of at least one chemoattractant substance to the first portion of said receptacle;

(d) adding said at least one *C. elegans* to said second portion of said receptacle; and (e) detecting, after a suitable time period, the behavioral response of said at least one *C. elegans* to said at least one test substance.

Point sources of substances could also be used to test chemorepulsion and/or chemoattraction. The square plate assay is an example of a point source assay used to measure both chemoattraction and chemorepulsion. See Troemel, et al., supra. Two spots of test substance are placed on the surface at one end of a square agar plate. Two spots of a control substance are placed at the other end, and a test population of C. elegans is placed in the center of the plate. After a suitable time period, the distribution of animals on the plate is quantitated. If the test substance is chemoattractive, the animals will tend to move toward that end of the plate. If the test substance is chemorepulsive, the animals will move away from that end of the plate. Although a square plate facilitates quantitation of the animals, the shape is not important for behavior. Point sources of substances could be used with round plates, for example. Like the chemorepulsive assay described previously, this assay could be used in conjunction with receptor expression from pCEASH2.1. In addition, this assay could be used with other vectors that drive expression in neurons mediating water-soluble chemoattractive behavior, or chemotactic behavior toward volatile compounds.

In addition to previously described assays, we propose three novel variations that are particularly preferred embodiments of the invention. First, presentation of substances as point sources can be used to assay large numbers of test substances by creating an array of spots of at least one test substance on a substrate medium. See FIG. 2. A number of different test substances can be placed in an array of spots on a plate. A test population of transgenic C. elegans created, as described above, can then be introduced and assayed to determine their chemotactic preference for the test substances. Spots of test substances that the C. elegans preferentially avoid, or are attracted to, would then be candidates for substances that modify the activity of human 7TMRs that are expressed in the sensory neurons of the test population of C. elegans. In a particularly preferred embodiment of the instant invention, the test substances can easily diffuse in the substrate medium. Presenting test substances as an array of point sources confers the advantage of being able to rapidly assay a large number of different point sources of substance for their effect on chemotactic behavior.

Example 2, detailed below, demonstrates a chemotactic assay using a simple array of substances. In this experiment, four different substances were placed in spot on a agar substrate. One substance, isoamyl alcohol, is a known strong chemoattractant to wildtype C. elegans. Bargmann, supra. A test population of wildtype C. elegans was then placed at the center of the petri dish, equidistant from each of the substances. The position of the animals was photographed at the initial time they were placed on the substrate and at a later time. As can be seen, at the later time point, the animals preferentially moved to the location of the strong chemoattractant. In a particularly preferred embodiment of our invention, the test population can be transgenic for a 7TMR gene, and the test substances can be molecules that potentially modify the activity of the receptor, as discussed above.

In yet another particularly preferred embodiment of the invention, microorganismal colonies, such as bacteria, viruses or yeast, are used as the point sources of test substances. A large number of techniques exist to create "libraries" of substances expressed by microorganisms. Cesareni, et al., Comb Chem High Throughput Screen 2(1): 1–17 (1999); Georgiou, et al., Nat Biotechnol. 15(1): 29–34 (1997); Sambrook, et al., 12. Screening Expression Libraries with Antibodies and Oligonucleotides. In Sambrook J, Fritsch E F, and Maniatis, T (eds), MOLECULAR CLONING: A LABORATORY MANUAL, Cold Spring Harbor Laboratory Press, Cold Spring Harbor, N.Y. (1989). These libraries can be used in our inventive methods to identify specific test substances that modify activity of the human 7TMRs expressed in the test population of C. elegans. For example, microorganismal colonies, each of which secrete a different substance, can be placed on the substrate medium. A test population of C. elegans can then be introduced onto the substrate. The behavioral preference of the animals to these colonies would indicate potential activity of the substance secreted by the colony on the human 7TMR(s) expressed in the test population.

Yet another particularly preferred embodiment of the invention is a chemotaxis assay that places a test population of C. elegans on a biomolecular separation matrix. Such a biomolecular separation matrix could be in agarose or polyacrylamide, and the animals could then be placed on the matrix. By monitoring the behavior of the animals, any preference for certain areas of the matrix could be determined. For example, a tissue that might contain a ligand for a human 7TMR could be fractionated by molecular mass in a matrix-based separation system. The chemotactic behavior of animals that express the human 7TMR in their sensory neurons could then indicate in what region of the matrix contained the ligand of the human 7TMR, and therefore, what mass the ligand was.

There are a large variety of separation techniques for biological samples, including those for small peptides, proteins, DNA, and other biological components. Many of these techniques use a matrix substrate that is amenable to a chemotaxis assay using test populations of C. elegans. For example, nucleic acids and proteins can be separated in a simple agarose substrate. Sambrook, et al., 6. Gel Electrophoresis of DNA, In Sambrook J, Fritsch E F, and Maniatis, T (eds), MOLECULAR CLONING: A LABORATORY MANUAL, Cold Spring Harbor Laboratory Press, Cold Spring Harbor, N.Y. (1989); Sambrook, et al, 18 Detection and Analysis of Proteins Expressed from Cloned Genes. In Sambrook J, Fritsch E F, and Maniatis, T (eds), MOLECULAR CLONING: A LABORATORY MANUAL, Cold Spring Harbor Laboratory Press, Cold Spring Harbor, N.Y. (1989). Once the separation is complete, a test population of C. elegans can be introduced onto the separation matrix. Behavioral preference for, or avoidance of, different regions of the matrix would indicate the presence of a substance at that location that modifies the activity of human 7TMR(s) expressed in the chemosensory neurons. The measurement of chemotactic behavior involves determining the spatial distribution of a test population of transgenic C. elegans of the instant invention at an initial time point and at a later timepoint when the test population is exposed to at least two spatially distinct concentrations of a substance. Methods for assaying the distribution of C. elegans have already been described. See Bargmann, supra; Troemel, et al., Cell 91:161–169 (1997); Jansen, et al., supra. In addition to these methods, we describe two embodiments of the instant invention that determine the spatial distribution of animals in the application of the inventive screening methods disclosed herein.

The animals may be detected by direct observation. For example in the water-soluble chemorepulsive assay, described above, an initial population of animals is placed at a defined location. After a suitable time period, the position of the animals is determined by direct observation of the agar surface using a suitable optical instrument. A chemotactic index can then be defined as the fraction of animals on the half of the petri plate containing the test substance (number of animals on test substance/total number of animals). The chemotactic index for the test substance can then be compared to the indices determined for compounds for which chemotactic behavior has been defined.

An alternative to direct observation is mechanical detection of the animals. For instance, such detection could involve the determination of optical density across the test surface by a machine. The animals would be detected by changes in density at the location where an animal was located. Alternatively, if the animals are expressing a reporter gene that can be detected in living animals (i.e., GFP), a machine could monitor the position of the animals using a suitable reporter gene detection protocol.

In a particularly preferred embodiment of the invention, determining spatial distribution of the transgenic *C. elegans* involves assaying the feeding behavior of the animals. Soil nematodes, such as *C. elegans*, typically feed on bacteria, and it is possible to grow *C. elegans* on a variety of bacterial species. Venette, et al., *Soil Biology and Biochemistry* 30: 949–960 (1998). In a preferred embodiment of the invention, such bacteria are selected from the group consisting of: *Acinetobacter calcoaceticus, Bacillus cereus, Bacillus* sp., *Enterobacter amnigenus, Enterobacter cloacae, Escherichia coli, Flavobacterium* sp., *Proteus vulgaris, Pseudomonas aeruginosa, Pseudomonas cepacia, Pseudomonas maltophilia, Pseudomonas putida, Pseudomonas* sp., *Serratia liquefaciens, Serratia marcesens, Zymobacillus macerans.* In the laboratory, strains of nematodes, including *C. elegans*, are customarily grown on uniform "lawns" of *E. coli* bacteria placed on an agar surface. Epstein, et al., *CAENORHABDITIS ELEGANS:* MODERN BIOLOGICAL ANALYSIS OF AN ORGANISM, Academic Press, San Diego, Calif. (1995).

As the *C. elegans* grow and reproduce, the *E. coli* lawn is diminished until no bacteria remain. Therefore, the reduction of the bacterial lawn is a measurement of an actively feeding population of *C. elegans*. The rate of decrease of the lawn is proportional to the number of feeding animals present. Example 3, below, demonstrates this assay. The consumption of bacteria can be used as an indirect indicator of the distribution of animals. Substances can be spotted onto a substrate in an array, and a uniform lawn of bacteria placed on the substrate, overlaying the array. A test population of *C. elegans* can be introduced and incubated for a suitable time period to allow consumption of the lawn. If the animals are attracted to a substance, then they will move to that region of the substrate and the bacterial lawn will be diminished at that spot in comparison to the surrounding lawn. Conversely, if a substance repels the animals, then the bacterial lawn at that spot will not be consumed. Thus, bacterial consumption can be used to assay the growth and location of a population of nematodes. If a GFP-expressing bacterial strain is used (Chalfie, et al., supra) as was done in the experiment of Example 3, the variations in bacterial density can be easily detected, for example, by photographing fluorescence intensity.

In another particularly preferred embodiment of the invention, chemotactic behavior of the transgenic *C. elegans* is assayed by combining the ability of *C. elegans* to consume bacteria with the ability to generate recombinant libraries of substances in bacteria, as discussed above. For instance, a library of secreted substances can be engineered through recombinant DNA methods in bacteria. Georgiou, et al., supra. The library can be plated out as individual colonies on an agar substrate, with each colony secreting a different substance. A test population of *C. elegans* could then be introduced onto the substrate. With no chemotactic preference shown by the animals, the colonies can be consumed at the same rate. However, if one or more of the colonies expressed a substance that was chemorepulsive to the animals, then that colony or colonies can be consumed at a slower rate. These "resistant" colonies could then be recovered and the substance identified through analysis of the bacterial clone.

Thus, in a particularly preferred embodiment, the instant invention provides a method for identifying at least one ligand of a human 7TMR said method comprising the steps of:

(a) providing at least one *C. elegans* that expresses a human 7TMR in the sensory neurons that correlate with behavior;

(b) at least two different concentrations of at least one test substance onto a substrate surface that contains growth medium;

(c) placing a uniform lawn of bacteria onto the surface of said growth medium;

(d) contacting said at least one *C. elegans* with the said uniform lawn of bacteria; and (e) detecting, after a suitable time period, a decrease in the density of said uniform lawn of bacteria.

The dauer pathway is an alternative life cycle stage common to many nematode species. Riddle, et al., supra. The dauer pathway is normally triggered by environmental stresses such as starvation, temperature extremes, or overcrowding. Genetically, the dauer pathway has been most intensively studied in *C. elegans*. The response to overcrowding in *C. elegans* is mediated by a substance known as dauer pheromone, which is secreted by the animals. When dauer pheromone becomes sufficiently concentrated, it triggers commitment to the dauer alternative life cycle stage. Riddle, et al., supra. Three sensory neurons have role in the appropriate response to dauer pheromone: ADF, ASI, and ASJ neurons. Bargmann, supra. In addition to pheromone, activation of a transgenically expressed human 7TMR in these neurons of *C. elegans* would be expected to lead to commitment to the dauer pathway. Unlike chemotaxis assays, measuring dauer formation does not require presentation of substances on a substrate that allows movement of *C. elegans*, nor does it require that the substance be present at two spatially distinct concentrations. Preferably, the test population of *C. elegans* are exposed to the substance during the portion of the life cycle at which commitment to the dauer pathway is made. Riddle, et al., supra. Measurement of dauer formation has been previously described. Id.

Thermotaxis chemosensory behavior can be used to assay the function of human 7TMRs that might be affected by temperature. A test population of *C. elegans* can be generated as described above that express a human 7TMR in the AFD neuron. The AFD neuron mediates thermotaxis, and expression of a thermoreactive human 7TMR in this neuron can modify the thermotactic behavior of the test population of *C. elegans*. The test population of animals can then be placed on a solid substrate that is maintained in a thermal gradient, as described (Bargmann, supra). The preference of the test population for certain thermal isoclines on the substrate can be used as a measure of human 7TMR activation.

In a particularly preferred embodiment of the invention, the chemosensory behavior of *C. elegans* can be used to identify substances that activate human 7TMRs. As outlined above, human 7TMRs can be expressed in *C. elegans*, and the *C. elegans* can then be exposed to an array of substances. By comparing the chemosensory behavior seen in test populations of wildtype animals (non-transgenic) and transgenic animals expressing a particular human 7TMR, substances can be identified that alter the behavior of only the transgenic *C. elegans*. These substances would then be candidates for interacting with and/or modifying the activity of the transgenically-expressed human 7TMR. Thus, a particularly preferred embodiment of the invention encompasses screening for substances that can activate human 7TMRs that have no known ligand, which are referred to in the art as "orphan receptors". This will be especially important in light of determination of the human genome sequence. Orphan 7TMRs can be expressed in *C. elegans* and, as outlined above, an array of test substances could be exposed to the animals. The behavior of the animals will then indicate the presence of an activating substance or ligand.

In yet another preferred embodiment of the invention, the test substances are present in beads, and the medium is solid or semi-solid.

Thus, a particularly preferred embodiment of the instant invention provides a method for identifying at least one ligand of at least one human 7TMR, said method comprising the steps of:

(a) providing at least one *C. elegans* that expresses a human 7TMR in the sensory neurons that correlate with behavior;

(b) placing a medium in a receptacle;

(c) placing at least two different concentrations of at least one test substance in said receptacle;

(d) adding said at least one *C. elegans* to said receptacle; and (e) detecting, after a suitable time period, the behavioral response of said at least one *C. elegans* over the surface of said medium.

Using this approach, the instant invention would allow the inexpensive testing of a large number of substances. For example, once a transgenic strain of *C. elegans* is generated, large populations of transgenic *C. elegans* can be grown for chemotactic assays. Many substances can be tested by spotting them in a large array on the substrate medium, as discussed above. In addition, a large variety of substances created by recombinant DNA techniques in microorganisms can be assayed at once. Thus, our invention can be used to identify rare or novel substances that act on certain human 7TMRs. This ability will have special utility when analyzing the human 7TMRs identified only through analysis of DNA sequence.

In a particularly preferred embodiment of the invention, screening methods with the transgenic *C. elegans* can be used to evaluate the potency and specificity of substances on human 7TMR activity. A strain of *C. elegans* can be generated that expresses a particular human 7TMR upon which a substance is known to act. Structurally related substances could then be tested and compared in a chemotactic assay for their efficacy in eliciting a chemotactic response from the human 7TMR-expressing strain. Because chemotactic response is a result of receptor activation, the response can be used as a gauge for how well substances can activate the human 7TMR. For instance, structurally related compounds can be tested to determine which chemical differences are important in activating the human 7TMR and eliciting a chemosensory response. Such information is important in determining the structure/activity relationship of different substances, and can lead to an understanding of what part of the chemical structure is important for receptor activity.

For example, a group of 12 receptors might be known, one of which interacts with a substance. Four transgenic strains of *C. elegans* can be generated that express three human 7TMRs each. These strains can be assayed for chemosensory response to the substance. The three human 7TMRs in the responding strain can then be expressed in individual strains to identify the responding human 7TMR.

In yet another preferred embodiment, the instant invention can be used to identify a human 7TMR activated by a particular substance by generating transgenic strains of *C. elegans* that express more than human 7TMR, as discussed above. For example, a large group of human 7TMRs may be identified, one of which is activated by a particular substance. Transgenic strains of *C. elegans* can be generated that express overlapping subsets of the human 7TMR group. By testing the chemosensory behavior of these strains toward the substance, the subset of human 7TMRs common to the strains that respond to the substance can be identified. These human 7TMRs can be further subdivided and transgenic strains of *C. elegans* made to identify the particular human 7TMR that responds to the substance.

In a particularly preferred embodiment, the instant invention provides a method for evaluating the potency of human 7TMR activation by a known ligand, said method comprising the steps of:

(a) providing at least one *C. elegans* that expresses at least human 7TMR, in the sensory neurons that correlate with behavior, wherein said human 7TMR has a known ligand;

(b) contacting said at least one *C. elegans* with said ligand and at least one structurally related compound; and (c) detecting the behavioral response of said at least one *C. elegans* to said at least one structurally related compound; and (d) comparing the behavioral response of said at least one *C. elegans* to said ligand to the behavioral response of said at least one *C. elegans* to said at least one structurally related compound.

In yet another particularly preferred embodiment of the invention, screening methods can be used to identify an antagonizing substance that blocks the effect of a substance on human 7TMR. For example, if a ligand-receptor pair is already known, our invention can be used to screen for or evaluate the ability of substances to antagonize receptor activation by the ligand. The chemosensory response of animals to the ligand in the presence and absence of substances can be assayed. If a substance antagonizes receptor activation by the ligand, then the chemotactic response of the animals to the ligand will be abolished in the presence of antagonist. If the test substance agonizes ligand activation of the receptor, then the chemotactic response should be enhanced in the presence of the substance.

This particularly preferred embodiment of the invention provides a method for identifying at least one test substance that modulates the activation of at least one human 7TMR by a known ligand, said method comprising the steps of:

(a) providing at least one *C. elegans* that expresses a human 7TMR in the sensory neurons that correlate with behavior, wherein said human 7TMR has a known ligand;

(b) contacting said at least one *C. elegans* with at least one test substance in the presence of said ligand;

(c) measuring the alteration of behavior of said at least one *C. elegans* in response to said at least one test substance; and (d) determining whether said at least one test compound binds to and activates or inhibits the activation of said human 7MR by said ligand.

In addition to chemotactic behavior, many other *C. elegans* behaviors are regulated by a variety of neurons within the nervous system. We propose that these behaviors can be modified by expression of a human 7TMR within these neurons in the nervous system, and that the behavior modification can be applied to the identification and characterization of substances that activate the human 7TMR, as outlined in the Field of the Invention.

Large-scale functional evaluation of the *C. elegans* genome has defined a number of standard phenotypes that are easily scored by trained *C. elegans* biologists: exploded (Exp), dumpy (Dpy), long body (Lon), hyperactive movement (Hpr), paralyzed (Prl), molt defect (Mlt), sterile (Ste), sick (Sck), body morphology defect (Bmd), vulvaless (Vul), slow growth (Gro), egg laying defect (Egl), larval arrest (Lva), protruding vulva (Pvl), multiple vulva (Muv), sterile progeny (Stp), small (Sma), clear (Clr), blistered (Bli), high incidence of male progeny (Him), roller (Rol), larval lethal (Lvl), uncoordinated (Unc), embryonic lethal (Emb) (Maduro, et al., *Genetics* 141, 977–88 (1995); Piano, et al., *Current Biology* 10, 1619–22 (2000); Gonczy, et al., *Nature* 408, 331–6 (2000); Fraser et al., *Nature* 408, 325–30 (2000)). Of these phenotypes, four can directly result from modification of nervous system function by gene mutation or expression of modified proteins: Hpr, Prl, Egl, and Unc. For example, expression of activated G proteins in the nervous system can lead to an Egl phenotype; in addition, mutations in a number of human 7TMR signaling pathway proteins can lead to an Egl phenotype, or suppress the action of a second mutation that leads to the Egl (Wilkie, *Current Biology* 10, R853–6 (2000)). Therefore, expression and activation of a human 7TMR could perturb the *C. elegans* nervous system and manifest or modify these phenotypes. The phenotypic read-out could then lead to evaluation of substances that would alter human 7TMR activation.

The Hpr, Prl, Egl and Unc phenotypes have been well documented in the literature and standard methods have been described for each of these phenotypes. Hyperactive behavior (Mendel et al., *Science* 267, 1652–5 (1995)) can be scored by examining the tracks of individual animals as they move across a solid agar medium. Hyperactive animals tend to have a "loopier" movement. The Paralyzed phenotype (Prl) is self-explanatory; the animals are capable of very little movement and tend to remain in one place for a long period of time (Saifee, et al., *Molecular Biology of the Cell* 9, 1235–52 (1998)). Animals exhibiting Egl, or egg laying, phenotype typically lay fewer eggs than normal. A severe Egl animal lays very few eggs and eventually is consumed by progeny that hatch within the animal (Wang et al., *Current Topics in Developmental Biology* 51, 189–220 (2001)). There are a large variety of Uncoordinated (Unc) phenotypes (Sulston, W B (ed), THE NEMATODE *CAENORHABDITIS ELEGANS*, Cold Spring Harbor Laboratory Press, Cold Spring Harbor, N.Y., (1988)). In general, uncoordinated behavior can be any deviation from the smooth sinusoidal movement and reaction to prodding exhibited by a normal animal. The movement defects seen in the Hpr, Prl and Unc phenotypes have obvious links to the animals' nervous systems. A correctly functioning neural network is required to produce smooth movements and responses to stimuli in the environment. The Egl phenotype can result from defects in a set of neurons called the HSNs, which inervate the egg-laying muscles. All of these phenotypes are well-characterized and can readily be identified by a trained *C. elegans* biologist (Sulston, W B (ed), THE NEMATODE *CAENORHABDITIS ELEGANS*, Cold Spring Harbor Laboratory Press, Cold Spring Harbor, N.Y., (1988)).

Perturbation of the *C. elegans* nervous system by a human 7TMR requires expression of the receptor of interest within the animal's nervous system. Such expression can be accomplished by fusing a DNA promoter segment that directs expression throughout the nervous system, i.e., in all neurons (pan-neuronal expression), to a DNA segment that encodes the human 7TMR. The promoter of the unc-119 gene is a well-characterized example of a pan-neuronal promoter (Maduro, et al, supra). Example 4 details the construction and use of a plasmid that will drive pan-neuronal expression of a human 7TMR using the unc-119 promoter DNA segment. This plasmid can be introduced via standard methods to produce a transgenic strain of *C. elegans* that express a human 7TMR throughout the nervous system (Mello, et al., *EMBO Journal* 10, 3959–70 (1991); Praitis et al., *Genetics* 157, 1217–26 (2001)). The resulting strains can then be examined for phenotypes, as detailed above.*C. elegans* Expression of a human 7TMR in the *C. elegans* nervous system can cause a phenotype-producing perturbation in at least three ways. First, the human 7TMR might be activated in one or many neurons by an endogenous ligand that is produced by the nematode. Activation of the receptor would lead to modification of neuronal function, thereby leading to an altered phenotypic state that can be assayed (see above). Second, the human 7TMR might be activated by an exogenously applied substance, again leading to modification of neuronal function and a resulting phenotype. Third, although not activated, the human 7TMR might associate with accessory proteins, such as human G proteins, thereby modifying neuronal function and leading to a phenotype in the transgenic animal.

Phenotypes induced by any of the three mechanisms detailed above can be used to evaluate substances, as detailed in the Field of the Invention. For example, if a human 7TMR is activated by an endogenous ligand to produce a phenotype, that phenotype can be used to screen for and identify substances that would antagonize the receptor. Specifically, a strain of animals that express a certain receptor might exhibit a phenotype due to activation by an endogenous ligand. An exogenous substance that would block activation of the 7TMR would be able to suppress, or return to normal, the phenotype. To find such antagonistic substances, the strain expressing the human 7TMR could then be cultured in the presence of a variety of substances to see which would suppress the phenotype. These substances would then be candidates for molecules that would antagonize human 7TMR activation. Because the phenotypic assay does not involve chemotaxis behavior as described previously, the substances would not have to be spatially distributed and could be uniformly distributed in the medium.

In addition to identifying antagonistic substances, molecular genetic techniques could be used to identify a surrogate, ligand present in a human 7TMR-expressing strain that exhibits a phenotype. For example, a human 7TMR-expressing strain could be subjected to mutagenic screens to identify mutations that would suppress the phenotype. Such mutations would be candidates for lesions that eliminate production of the endogenous ligand. The mutations could be genetically mapped and molecularly cloned. Such suppressor genetic screens are commonly used in the field of genetics in a variety of contexts (Dong, et al., *Genes & Development* 14, 2003–14 (2000)). Mapping and cloning techniques for mutations are also well-known and characterized (Wicks et al., *Nature Genetics* 28, 160–4 (2001)).

Human 7TMR-expressing strains of *C. elegans* could also be used to find substances that would activate, or agonize, the receptor. For example, a strain of nematodes expressing a human 7TMR might not exhibit a phenotype because no endogenous ligand produced by the receptor-expressing strain activates the receptor. However, an exogenously applied agonistic substance that activated the human 7TMR might cause a receptor-expressing strain of nematodes to exhibit a phenotype. Therefore, agonistic substances could be identified by culturing the human 7TMR-expressing strain in the presence of a variety of substances to see if such exposure leads to a phenotype. Substances identified in this way would be candidates for molecules that bind to and activate the human 7TMR.

A human 7TMR-expressing strain that exhibits a phenotype upon exposure an agonistic substance could be used to evaluate the specificity and efficacy of different substances. For example, structurally related substances could be evaluated for their effectiveness by comparing how well they elicit a phenotype from the same human 7TMR-expressing strain. Likewise, a human 7TMR-expressing strain that exhibits a phenotype suppressable by an exogenously applied antagonist could be used to evaluate different antagonistic substances. Thus, human 7TMR-expressing strains would provide a means to evaluate the specificity and efficacy of substances that interact with the human 7TMRs.

In summary, the invention proposes that expression of human 7TMRs within the neurons of *C. elegans* can modify behaviors and create phenotypes. These behaviors and phenotypes are useful for the identification of agonist and antagonist substances that act on the human 7TMRs. In addition, the behaviors and phenotypes are useful for the evaluation of specificity and efficacy of substances that interact with human 7TMRs.

EXAMPLES

Example 1

DNA Construct for Production of Transgenic Nematodes that Express Cell Surface Receptors:

FIG. 1 diagrams a constructed plasmid, named pCEASH2.1, capable of driving expression in the ADL and ASH neurons of *C. elegans* that mediate water-soluble chemorepulsion. Basepairs 1–7 correspond to the unique Kpn I site in the multiple cloning sites (MCS) region of the plasmid pBSKS(+) (Stratagene; Genbank Accession Number X52331). Basepairs 7–2830 correspond to nucleotides 31002 to 33825 in the sequence of cosmid C16A11 (Genbank Accession Number AF077536), with the exception that nucleotides 33818–33825 have been altered to read "CCATGGCC". This 2824 basepair DNA segment corresponds to the promoter region of the *C. elegans* gpa-11 gene, up to and including the start methionine codon. The alterations to the sequence result in the introduction of a NcoI site at the start codon of the gpa-11 protein coding region. Basepairs 2831 to 2907 correspond to the MCS region of pBSKS(+), from the unique Xho I site to the unique Not I site. Basepairs 2908 to 4178 correspond to basepairs 30364 to 29100 in the sequence of cosmid F32A7 (Genbank Accession Number Z83107), except for the addition of the sequence "AATT" at position 29553 in the F32A7 sequence (this change eliminates an EcoRI site). This DNA segment contains the last 15 codons of the *C. elegans* unc-54 protein coding region, followed by 1228 basepairs of DNA 3' to the unc-54 stop codon. This region provides transcriptional termination and mRNA processing signals. Jansen, et al., supra. Nucleotides 4179 to 7036 correspond to the pBSKS (+) plasmid from the unique Sac I site in the polylinker up to, but not including, the unique Kpn I site. In summary, pCEASH2.1 contains the *C. elegans* gpa-11 promoter sequence fused to the MCS of the pBSKS(+) plasmid, followed by the 3' region of the *C. elegans* unc-54 gene.

When introduced into *C. elegans*, the open reading frame located between the gpa-11 initiation codon and the unc-54 stop codon is expressed in the ASH and ADL chemosensory neurons. A heterologous sequence can be introduced into this reading frame using the unique sites contained in the MCS of pCEASH2.1. If a human 7TMR protein coding sequence is engineered with an NcoI site at the start methionine, it can be fused to the gpa-11 start methionine such that translational initiation will occur at the start methionine of the inserted sequence. In this way, the authentic peptide signal sequence of a receptor can be maintained as discussed above, while the appropriate DNA regulatory elements are introduced to direct expression of the human 7TMR protein in the ASH and ADL sensory neurons.

Example 2

Chemotaxis Assay

Figure 2:
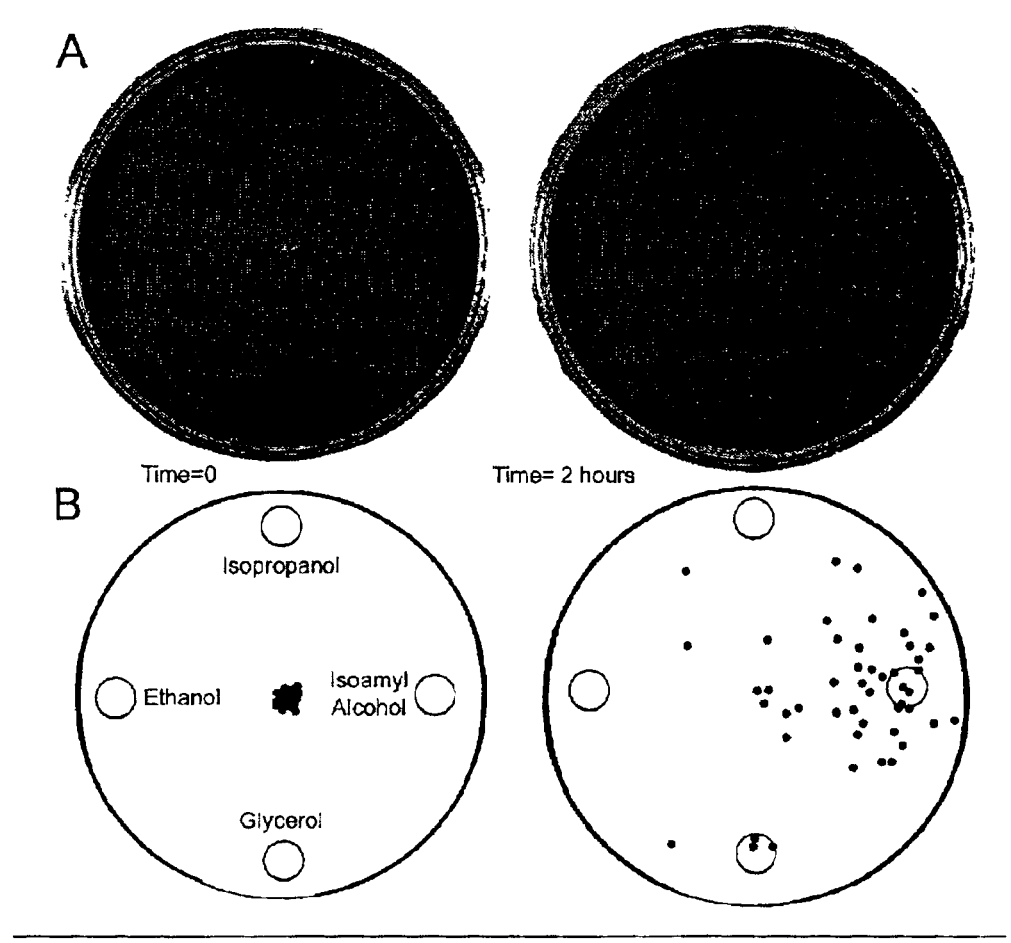
FIG. 2 demonstrates a nematode chemotaxis assay using an array of test substances. A round petri plate has been filled with an solid agar substrate. Test substances were spotted as indicated in panel B. A test population of C. elegans was placed in the center of the plate (see leftmost panels). The distribution of animals was determined at the initial time, and after 2 hours by visual inspection of the plate. The plate was also recorded by digital photography at the initial and 2 hour timepoints for this figure. In panel A, the actual digital photomicrographs are displayed. In panel B, the positions of the animals and the test substances is schematized based on the digital photomicrographs. The test population shows a clear preference for the spot of isoamyl alcohol.

FIG. 2 depicts a simple demonstration of a chemotaxis assay using an array of substances. In panel A, images of the experiment are shown. In panel B, a schematic of the images are drawn, with the positions of the test animals marked with black dots. The substrate is composed of a 0.5 cm. thick solidified agar solution (Troemel, et al., supra.) poured in a petri dish that is 10 cm. in diameter. 4 microliter samples of the substances labeled in the schematic were placed equidistant from the center of the agar surface. A test population of *C. elegans* animals was placed in the center of the agar surface. Images were taken at the initial time and two hours after placement of the test population. The position of the animals at the two times is diagrammed in FIG. 2. After two hours, the animals have preferentially moved toward the spot of isoamyl alcohol, a strong chemoattractant. Panel B depicts this movement.

Example 3

Bacterial Consumption of a Culture of GFP-expressing Bacteria by *C. elegans*

Figure 3:
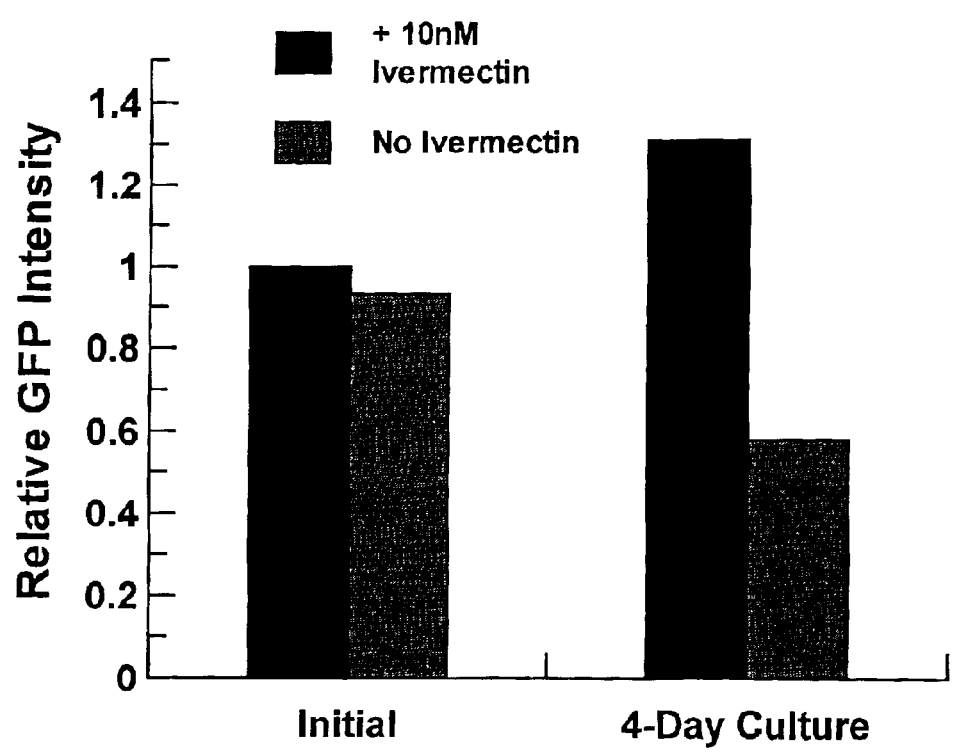
FIG. 3 demonstrates consumption of GFP-expressing bacteria by a culture of C. elegans. Two cultures of C. elegans and GFP-expressing bacteria were placed in microtiter wells. In one well, a lethal concentration of 10 nanomolar ivermectin was placed. The GFP fluorescence in the wells was determined by a fluorescent plate reader instrument at the initial time, and after two days of culture. Fluorescence is displayed as Relative Intensity normalized to the fluorescent intensity present in the initial ivermectin-containing well. Notably, in the ivermectin-containing well, in which the C. elegans animals are dead, GFP fluorescence increases as the bacteria grow. In contrast, the non-ivermectin well shows a decrease in GFP fluorescence as the C. elegans population consumes the bacteria.

In this experiment, GFP-expressing bacteria are placed in two microtiter wells along with a population of *C. elegans*. Because the bacteria express GFP, the amount of bacteria can easily be assayed using a fluorescent plate reader (Cytoflour, Perspective Biosystems). In one well, the medium also contains ivermectin, a nematocidal compound that kills *C. elegans*. Initially, both wells show equivalent levels of bacteria. However, after 4 days of culture, the bacteria in the well lacking ivermectin has been reduced, while the ivermectin-containing well shows bacterial growth. FIG. 3 depicts this experiment. Thus, bacterial consumption can be used to assay the growth and feeding of a population of nematodes. If a GFP-expressing bacterial strain is used (Chalfie, et al., supra) as was done in the experiment shown in FIG. 3, the variations in bacterial density can be easily visualized by photographing fluorescence intensity.

Example 4

Figure 4:
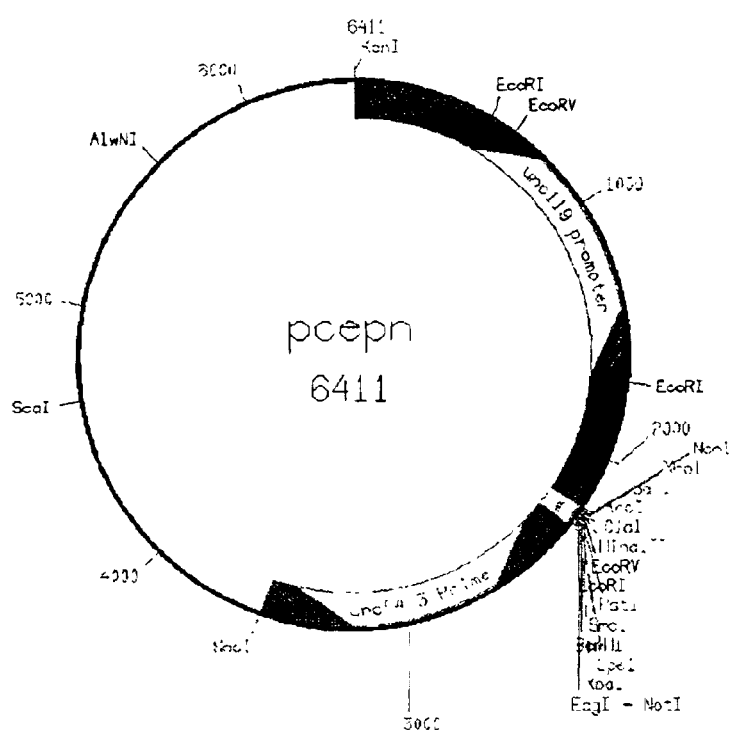
FIG. 4 diagrams the pCEPN plasmid, which is capable of driving expression in the nervous system of C. elegans, as described in Example 4. In brief, the promoter region of the unc-119 gene has been placed in a plasmid context with the 3' region of the unc-54 gene (see example 4 text for a detailed description). This unc-119 promoter region is sufficient to drive expression in the C. elegans nervous system.

DNA Construct for Production of Transgenic *C. elegans* that Express Human 7TMRs within the Nervous System:

FIG. 4 diagrams a constructed plasmid, named pCEPN, capable of driving pan-neuronal expression in *C. elegans*.

Basepairs 1–7 correspond to the unique Kpn I site in the multiple cloning sites (MCS) region of the plasmid pBSKS (+) (Stratagene; Genbank Accession Number X52331). Basepairs 7–2205 correspond to nucleotides 1318 to 3516 in the sequence of C. elegans cosmid M142 (Genbank Accession Number Z73428), with the exception that nucleotides 3509–3516 have been altered to read "CCATGGCC". This 2199 basepiar DNA segment corresponds to the promoter region of the C. elegans unc-119 gene, up to and including the start methionine codon (Maduro, Pilgrim, Genetics 141, 977–88 (1995)). The alterations to the sequence result in the introduction of a NcoI site at the start codon of the unc-119 protein coding region. Basepairs 2206 to 2282 correspond to the MCS region of pBSKS(+), from the unique Xho I site to the unique Not I site. Basepairs 2283 to 3553 correspond to basepairs 30364 to 29100 in the sequence of cosmid F32A7 (Genbank Accession Number Z83107), except for the addition of the sequence "AATT" at position 29553 in the F32A7 sequence (this change eliminates an EcoRI site). This DNA segment contains the last 15 codons of the C. elegans unc-54 protein coding region, followed by 1228 basepairs of DNA 3' to the unc-54 stop codon. This region provides transcriptional termination and mRNA processing signals. Jansen, et al., supra. Nucleotides 3554 to 6411 correspond to the pBSKS(+) plasmid from the unique Sac I site in the polylinker up to, but not including, the unique Kpn I site. In summary, pCEPN contains the C. elegans unc-119 promoter sequence fused to the MCS of the pBSKS(+) plasmid, followed by the 3' region of the C. elegans unc-54 gene.

When introduced into C. elegans, the open reading frame located between the unc-119 initiation codon and the unc-54 stop codon is expressed pan-neuronally (Maduro, Pilgrim, Genetics 141: 977–88 (1995)). A heterologous sequence can be introduced into this reading frame using the unique sites contained in the MCS of pCEPN. If a human 7TMR protein coding sequence is engineered with an NcoI site at the start methionine, it can be fused to the unc-119 start methionine, such that translational initiation will occur at the start methionine of the inserted sequence. In this way, the authentic peptide signal sequence of a receptor can be maintained as discussed above, while the appropriate DNA regulatory elements are introduced to direct expression of the human 7TMR protein in all neurons of the transgenic animal.

Example 5

Figure 5:
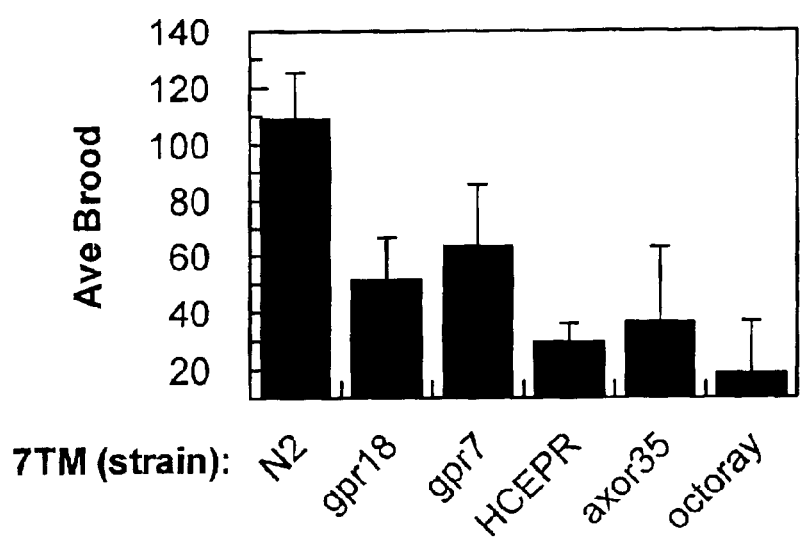
FIG. 5 illustrates Egl, or egg-laying, phenotypes produced by expression of human 7TMRs in the nervous system of C. elegans (see example 5 for a detailed description of receptors). In brief, 5–8 single transgenic animals were allowed to lay eggs for 40 hours. The number of eggs laied were counted and graphed. The N2 strain is the canonical wildtype non-transgenic C. elegans strain. The receptor-expressing strains are indicated below each bar by the name of the expressed receptor. In comparison to N2, most of the transgenic strains show a reduction in the number of eggs laid.

Egg-laying (Egl) Phenotype Produced by Expressing 7TMRs Pan-Neuronally in C. elegans DNA segments encoding six 7TMRs were cloned into the pCEPN expression vector (see Example 4). The five human 7TMRs are: GPR18 (SwissProt accession# Q14330), GPR7 (SwissProt accession# P48145), HCEPR (SwissProt accession# O00143), AXOR35 (SwissProt accession# Q9GZQ0), Octoray (tremble accession# Q9BY21). Transgenic C. elegans strains were created with the cloned receptor constructs using standard methods (Mello, et al., EMBO Journal 10, 3959–70 (1991)). 5–8 single adult transgenic animals were picked from each strain and allowed lay eggs for 40 hours. The adult animals were removed and the number of eggs laid was quantitated. FIG. 5 illustrates the results obtained. The normal, wildtype, strain of C. elegans, N2, laid 109 eggs, plus or minus 16, within the 40 hour period. In contrast, most of the human 7TMR-expressing strains reduce the number of eggs laid. In two cases, this Egl phenotype was relatively mild, with a reduction of around 50% in the number of eggs laid (GPR18—47% wildtype, GPR7—58% wildtype). However, two receptor-expressing strains showed a reduction in eggs laid of greater than 66% (HCEPR—27% wildtype, AXOR35—34% and Octoray—17%). In particular, Octoray exhibits a penetrant Egl phenotype, with Octoray-expressing animals laying less than 17% the normal number. This example shows that expression of non-nematode human 7TMRs in C. elegans can cause a scorable phenotype.

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof. Modifications and improvements of the embodiments specifically disclosed herein are within the scope of the following claims. Without further elaboration, one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A method for identifying at least one test substance that is an antagonist of a human 7 transmembrane receptor (h7TMR), said method comprising the steps of:
   (a) providing at least one transgenic C. elegans whose genome comprises a nucleotide sequence encoding a h7TMR, wherein said h7TMR is expressed in sensory neurons of said transgenic C. elegans, and wherein said sensory neurons correlate with behavior, and wherein said transgenic C. elegans exhibits a phenotype;
   (b) contacting said at least one transgenic C. elegans with at least one test substance, wherein said at least one test substance is distributed in a medium;
   (c) determining whether said at least one test substance causes a suppression of said phenotype in said at least one transgenic C. elegans; and
   (d) identifying said at least one test substance that causes a suppression of said phenotype in said at least one transgenic C. elegans as an antagonist of said 7TMR.

2. The method as claimed in claim 1, wherein said behavior is volatile chemoattraction, and said sensory neurons are AWA neurons.

3. The method as claimed in claim 1, wherein said behavior is volatile chemorepulsion, and said sensory neurons are AWB neurons.

4. The method as claimed in claim 1, wherein said behavior is water-soluble chemoattraction, and said sensory neurons are chosen from the group of: ASE, ADF, ASG, and ASI neurons.

5. The method as claimed in claim 1, wherein said behavior is water-soluble chemorepulsion, and said sensory neurons are selected from the group consisting of: ASH and ADL neurons.

6. The method as claimed in claim 1, wherein said behavior is dauer formation, and said sensory neurons are selected from the group consisting of: ASI, ASG, and ADF neurons.

7. The method as claimed in claim 1, wherein said behavior is chosen from the group of: thermoattraction and thermorepulsion, and said sensory neurons are AFD neurons.

8. The method as claimed in claim 1, wherein the medium is chosen from the group of: buffer, growth medium, and agar.

9. The method as claimed in claim 1, wherein the medium is a growth medium that comprises a biomolecular separation in a matrix.

10. The method as claimed in claim 1, wherein said matrix is chosen from the group of: agarose and polyacrylamide.

* * * * *